United States Patent
McAlister

(10) Patent No.: US 9,297,530 B2
(45) Date of Patent: Mar. 29, 2016

(54) OXYGENATED FUEL

(71) Applicant: McAlister Technologies, LLC, Phoenix, AZ (US)

(72) Inventor: Roy E. McAlister, Phoenix, AZ (US)

(73) Assignee: McAlister Technologies, LLC, Phoenix, AZ (US)

(*) Notice: Subject to any disclaimer, the term of this patent is extended or adjusted under 35 U.S.C. 154(b) by 0 days.

(21) Appl. No.: 14/299,767

(22) Filed: Jun. 9, 2014

(65) Prior Publication Data
US 2015/0053161 A1    Feb. 26, 2015

Related U.S. Application Data

(63) Continuation of application No. 13/027,195, filed on Feb. 14, 2011, now Pat. No. 8,784,095.

(60) Provisional application No. 61/304,403, filed on Feb. 13, 2010.

(51) Int. Cl.
*F23N 5/00*     (2006.01)
*F23G 5/02*     (2006.01)
(Continued)

(52) U.S. Cl.
CPC ............... *F23G 5/02* (2013.01); *B01J 19/0006* (2013.01); *B01J 19/0013* (2013.01); *B01J 19/127* (2013.01); *B01J 19/1812* (2013.01); *B01J 19/20* (2013.01); *B01J 19/245* (2013.01); *C01B 3/02* (2013.01); *C01B 3/24* (2013.01); *C01B 3/26* (2013.01); *C10B 23/00* (2013.01); *C10B 53/02* (2013.01); *C10J 3/20* (2013.01); *C10J 3/72* (2013.01); *C10J 3/723* (2013.01); *F23G 7/00* (2013.01); *F24J 2/0007* (2013.01);
(Continued)

(58) Field of Classification Search
USPC .......................... 431/2, 12; 110/92, 210, 300
See application file for complete search history.

(56) References Cited

U.S. PATENT DOCUMENTS 2,180,626 A    11/1939    Delorme
3,698,882 A *   10/1972    Saas et al. ........................ 48/210
(Continued)

FOREIGN PATENT DOCUMENTS

JP    2005289856    10/2005
JP    2007314745    12/2007
(Continued)

OTHER PUBLICATIONS

Geologic Sequestration of Carbon Dioxide | UIC | US EPA. US Environmental Protection Agency. Accessed: Aug. 30, 2009. <http://www.epa.gov/safewater/uic/wells_sequestration.html>. pp. 1-5.
(Continued)

*Primary Examiner* — Avinash Savani
(74) *Attorney, Agent, or Firm* — Perkins Coie LLP

(57) ABSTRACT

Techniques, systems, apparatus and material are disclosed for generating oxygenated fuel. In one aspect, a method of producing an oxygenated fuel from biomass waste for use in a combustion system includes dissociating the biomass waste to produce one or more carbon donors. The biomass waste produced carbon donors are reacted with an oxygen donor to produce the oxygenated fuel comprising oxygenated carbon. Reacting the carbon donors with the oxygen donors includes applying waste heat recovered from an external heat source to the reaction of carbon donors and oxygen donor. The oxygenated fuel is combusted in the combustion system.

16 Claims, 6 Drawing Sheets

(51) Int. Cl.
| | |
|---|---|
| B01J 19/12 | (2006.01) |
| B01J 19/18 | (2006.01) |
| B01J 19/20 | (2006.01) |
| C01B 3/24 | (2006.01) |
| F24J 2/07 | (2006.01) |
| C01B 3/26 | (2006.01) |
| C10B 53/02 | (2006.01) |
| G01M 3/22 | (2006.01) |
| C10J 3/72 | (2006.01) |
| C10J 3/20 | (2006.01) |
| B01J 19/00 | (2006.01) |
| C01B 3/02 | (2006.01) |
| C10B 23/00 | (2006.01) |
| F23G 7/00 | (2006.01) |
| B01J 19/24 | (2006.01) |
| F24J 2/00 | (2014.01) |
| F24J 2/06 | (2006.01) |
| G01N 1/40 | (2006.01) |
| G01N 35/00 | (2006.01) |
| G01N 1/02 | (2006.01) |

(52) U.S. Cl.
CPC ............... *F24J 2/07* (2013.01); *G01M 3/223* (2013.01); *G01N 35/00871* (2013.01); *B01J 2219/00074* (2013.01); *B01J 2219/00085* (2013.01); *B01J 2219/00144* (2013.01); *B01J 2219/00162* (2013.01); *B01J 2219/00164* (2013.01); *B01J 2219/0801* (2013.01); *B01J 2219/0871* (2013.01); *B01J 2219/0875* (2013.01); *B01J 2219/1203* (2013.01); *B01J 2219/187* (2013.01); *B01J 2219/24* (2013.01); *C01B 2203/0266* (2013.01); *C01B 2203/04* (2013.01); *C01B 2203/0465* (2013.01); *C01B 2203/0485* (2013.01); *C01B 2203/0811* (2013.01); *C01B 2203/0822* (2013.01); *C01B 2203/0872* (2013.01); *C01B 2203/0883* (2013.01); *C10J 2300/1284* (2013.01); *C10J 2300/1665* (2013.01); *C10J 2300/1884* (2013.01); *C10J 2300/1892* (2013.01); *F24J 2/0023* (2013.01); *F24J 2/06* (2013.01); *G01N 1/405* (2013.01); *G01N 35/00613* (2013.01); *G01N 2001/021* (2013.01); *Y02B 10/20* (2013.01); *Y02E 10/41* (2013.01); *Y02E 50/14* (2013.01); *Y02E 50/32* (2013.01); *Y02E 60/324* (2013.01); *Y02E 60/364* (2013.01); *Y02E 60/366* (2013.01); *Y02T 10/16* (2013.01)

(56) References Cited

U.S. PATENT DOCUMENTS

| | | | | |
|---|---|---|---|---|
| 4,177,120 | A * | 12/1979 | Zenty | 204/157.47 |
| 4,339,546 | A | 7/1982 | Randalls | |
| 5,343,699 | A | 9/1994 | McAlister | |
| 5,492,624 | A * | 2/1996 | Rozich | 210/605 |
| 5,882,484 | A | 3/1999 | Pyy | |
| 6,024,032 | A * | 2/2000 | Sharpe | 110/342 |
| 6,133,328 | A | 10/2000 | Lightner | |
| 6,155,212 | A | 12/2000 | McAlister | |
| 6,270,731 | B1 * | 8/2001 | Kato et al. | 422/177 |
| 6,446,597 | B1 | 9/2002 | McAlister | |
| 6,890,419 | B2 | 5/2005 | Reichman et al. | |
| 7,033,570 | B2 | 4/2006 | Weimer et al. | |
| 7,033,822 | B2 | 4/2006 | Maston | |
| 7,132,090 | B2 | 11/2006 | Dziedzic et al. | |
| 7,138,046 | B2 | 11/2006 | Roychowdhury et al. | |
| 7,169,821 | B2 | 1/2007 | Branson | |
| 7,309,435 | B2 | 12/2007 | Rozich | |
| 7,425,315 | B2 | 9/2008 | Kruesi | |
| 7,482,078 | B2 | 1/2009 | Sridhar et al. | |
| 7,491,453 | B2 | 2/2009 | Logan et al. | |
| 7,507,341 | B2 | 3/2009 | Gallagher et al. | |
| 7,562,708 | B2 | 7/2009 | Cogliandro et al. | |
| 7,569,203 | B2 | 8/2009 | Fridman et al. | |
| 7,572,369 | B2 | 8/2009 | Gallagher et al. | |
| 7,572,530 | B2 | 8/2009 | Gottmann et al. | |
| 7,575,822 | B2 | 8/2009 | Mitlitsky et al. | |
| 7,591,880 | B2 | 9/2009 | Levan et al. | |
| 7,599,760 | B2 | 10/2009 | Dutta et al. | |
| 7,608,439 | B2 | 10/2009 | McTavish et al. | |
| 7,618,606 | B2 | 11/2009 | Fan et al. | |
| 7,628,137 | B1 | 12/2009 | McAlister | |
| 7,753,973 | B2 | 7/2010 | Galloway | |
| 7,878,131 | B2 | 2/2011 | Becchetti et al. | |
| 7,906,559 | B2 | 3/2011 | Olah et al. | |
| 7,931,783 | B2 | 4/2011 | Dam-Johansen et al. | |
| 7,931,997 | B2 | 4/2011 | Gottmann et al. | |
| 7,947,155 | B1 | 5/2011 | Green et al. | |
| 8,022,260 | B2 | 9/2011 | O'Connor et al. | |
| 8,070,835 | B2 | 12/2011 | McAlister | |
| 8,212,088 | B2 | 7/2012 | Olah et al. | |
| 8,226,798 | B2 | 7/2012 | van Aardt et al. | |
| 8,318,997 | B2 | 11/2012 | McAlister | |
| 8,784,095 | B2 | 7/2014 | McAlister | |
| 8,912,239 | B2 | 12/2014 | McAlister | |
| 8,916,735 | B2 | 12/2014 | McAlister | |
| 8,975,458 | B2 | 3/2015 | McAlister | |
| 2002/0077401 | A1 | 6/2002 | Chaudhary et al. | |
| 2004/0253168 | A1 | 12/2004 | Chu | |
| 2006/0029893 | A1 * | 2/2006 | Hsu | 431/2 |
| 2006/0280669 | A1 | 12/2006 | Jones | |
| 2007/0056842 | A1 | 3/2007 | Roychowdhury et al. | |
| 2007/0099038 | A1 | 5/2007 | Galloway | |
| 2008/0233029 | A1 | 9/2008 | Fan et al. | |
| 2008/0264771 | A1 | 10/2008 | Dam-Johansen et al. | |
| 2009/0007484 | A1 | 1/2009 | Smith | |
| 2009/0020405 | A1 * | 1/2009 | Fan et al. | 201/12 |
| 2009/0183430 | A1 | 7/2009 | Schubert et al. | |
| 2009/0202413 | A1 | 8/2009 | Saxena | |
| 2009/0208784 | A1 | 8/2009 | Perry et al. | |
| 2009/0208785 | A1 | 8/2009 | McElroy | |
| 2009/0246596 | A1 | 10/2009 | Sridhar et al. | |
| 2009/0269626 | A1 | 10/2009 | Mitlitsky et al. | |
| 2009/0273240 | A1 | 11/2009 | Gurunathan et al. | |
| 2009/0280360 | A1 | 11/2009 | Weingaertner et al. | |
| 2009/0291346 | A1 | 11/2009 | Hickey et al. | |
| 2010/0275823 | A1 | 11/2010 | Pahls | |
| 2010/0298450 | A1 | 11/2010 | Datta et al. | |
| 2011/0036320 | A1 | 2/2011 | Peret | |
| 2011/0070510 | A1 | 3/2011 | McAlister | |
| 2013/0205647 | A1 | 8/2013 | MAlister | |
| 2014/0342417 | A1 | 11/2014 | McAlister | |
| 2014/0356744 | A1 | 12/2014 | McAlister | |
| 2015/0110683 | A1 | 4/2015 | McAlister | |
| 2015/0191354 | A1 | 7/2015 | McAlister | |

FOREIGN PATENT DOCUMENTS

| | | |
|---|---|---|
| JP | 2010031187 | 2/2010 |
| WO | 2007122498 | 11/2007 |
| WO | 2009002191 | 12/2008 |
| WO | 2011100695 | 8/2011 |

OTHER PUBLICATIONS

NETL: What Is Carbon Sequestration? US Department of Energy—National Energy Technology Laboratory. Accessed: Aug. 30, 2009. <http://www.netl.doe.gov/technologies/carbon_swq/FAQs/carbon-seq.html>. 5 pages.

US EPA—Carbon Sequestration in Agriculture and Forestry: Frequently Asked Questions. US Environmental Protection Agency. Published: Oct. 19, 2006. Accessed: Aug. 30, 2009. <http://www.epa.gov/sequestration/faq.html>. 5 pages.

Colls, Alison. "Carbon Sequestration." Environmental Change Institute. Accessed: Aug. 30, 2009. <http://climatex.org/articles/climate-change-info/carbon-sequestration/>. pp. 1-4.

(56) References Cited

OTHER PUBLICATIONS

European Search Report for Application 11742988.6; Report Dated Dec. 19, 2013; 10 pages.

International Search Report and Written Opinion for PCT Application No. PCT/US2011/024771; Applicant: McAlister Technologies, LLC; Date of Mailing: Feb. 14, 2011; 8 pages.

International Search Report and Written Opinion for PCT Application No. PCT/US2011/024800; Applicant: McAlister Technologies, LLC; Date of Mailing: Oct. 20, 2011; 12 pages.

International Search Report and Written Opinion for PCT Application No. PCT/US2011/024801; Applicant: McAlister Technologies, LLC; Date of Mailing: Oct. 31, 2011; 10 pages.

Richard, Michael Graham. "Important! Why Carbon Sequestration Won't Save Us." TreeHugger. Published: Jul. 31, 2006. <http://treehugger.com/files/2006/07/carbon_sequestration.php>. pp. 1-6.

Salleh, Anna. "Urea 'Climate Solution' May Backfire." ABC.net.au. Published: Nov. 9, 2007. Accessed: Aug. 30, 2009. <http://www.abc.netau/science/articles/2007/11/09/2085584.htm>. pp. 1-3.

* cited by examiner

OXYGENATED FUEL

CLAIM OF PRIORITY

The present application is a continuation of U.S. application Ser. No. 13/027,195, filed Feb. 14, 2011, now U.S. Pat. No. 8,784,095, and titled OXYGENATED FUEL, which claims priority to and the benefit of U.S. Patent Application No. 61/304,403, filed on Feb. 13, 2010 and titled FULL SPECTRUM ENERGY AND RESOURCE INDEPENDENCE, which applications are incorporated herein by reference in their entireties. To the extent the foregoing applications and/or any other materials incorporated herein by reference conflict with the disclosure presented herein, the disclosure herein controls.

BACKGROUND

This application relates to devices, techniques and materials related to biofuels.

In general, fossil fuels in modern engines provide incomplete combustion and create adverse heat transfers, particularly in automotive engine applications. In large part, this is because conventional operation of engines provides for homogeneous-charge combustion and allows quenching of fuels undergoing combustion with consequent heat losses to the piston, cylinder walls, and head components along with pollutive emissions. After quenching of combustion, partially burned fuel constituents pass out of the combustion chamber to the exhaust system to cause further efficiency losses and pollution of the atmosphere. In both homogeneous-charge and diesel engine operations, liquid fuel droplets must be evaporated and depolymerized or "cracked" to promote combustion. These processes require heat from the air or from the combustion of other fuel constituents and considerable time for these events to be completed in order to complete the combustion process. About ⅓ of the heat released by combustion is lost through the cooling system of the engine and is dissipated to the environment through the radiator. Engines are designed to open the exhaust valve when the hot combustion gases still have considerable pressure and thus substantial amounts of heat and pressure potential energy is lost through the exhaust system. About ⅓ of the heat released by combustion is lost through the exhaust system of the engine and is dissipated to the environment.

In order to provide for marginal relief from atmospheric pollution, fuel purveyors have promoted more complete combustion of fossil fuels by additions of supplements such as methyl tertiary butyl ether or "MTBE" a compound with the molecular formula $C_5H_{12}O$. However because of groundwater water contamination by MTBE a more recent practice has been to add ethanol a compound with the formula $C_2H_5OH$. The concentration of such oxygenated additives has been about 5% to 10% of the total fuel mixture. In practice it has been shown that such additions of oxygen at the carbon to oxygen ratio of 5:1 or 2:1 for a relatively small fraction of all the fuel molecules present in the combustion process helps promote more complete combustion by providing oxygen for oxidation of other fuel constituents. Nevertheless, considerable additional expense is incurred for catalytic reactors for attempts to marginally reduce air pollution from engines using hydrocarbon fuels with additions of ethanol. Such air pollution remains objectionable particularly in congested cities and can cause or exacerbate lung diseases, heart and circulatory problems, corrosion of construction materials and contributes to greenhouse gas accumulation problems.

SUMMARY

Techniques, structures, apparatus and materials are disclosed for generating oxygenated fuel for use in an engine to increase fuel efficiency and prevent damage to the engine cause by the combustion process.

In one aspect, a method of producing an oxygenated fuel from biomass waste for use in a combustion system includes dissociating the biomass waste to produce one or more carbon donors. The biomass waste produced carbon donors reacts with an oxygen donor to produce the oxygenated fuel that includes oxygenated carbon. Reacting the carbon donors with the oxygen donor includes applying waste heat recovered from an external heat source to the reaction of carbon donors and oxygen donor; and combusting the oxygenated fuel in the charge combustion system.

Implementations can optionally include one or more of the following features. The one or more carbon donors can include carbon, and reacting the one or more carbon donors with the oxygen donor can include partially oxidizing the carbon to produce carbon monoxide and carbon dioxide. The one or more carbon donors can include hydrocarbon and alcohol, and the oxygen donor can include steam. Also, reacting the one or more carbon donors with the oxygen donor can include reacting the hydrocarbon and alcohol with the steam to produce carbon monoxide and hydrogen. Combusting the oxygenated carbon in the combustion system can include providing multiple layers of an oxidant and the oxygenated fuel mixture in a combustion zone of the combustion system. The method can include controlling timing or duration of fuel injection using adaptive control. Also, the method can include controlling a fuel delivery pressure using adaptive control. The combustion system can include a stratified-charge combustion system.

In another aspect, a method of producing an oxygenated fuel from biomass waste for use in a combustion system includes dissociating the biomass waste under an anaerobic reaction to produce the oxygenated fuel comprising oxygenated carbon and hydrogen. The dissociating under the anaerobic reaction includes applying waste heat recovered from an external heat source to the biomass waste and combusting the oxygenated fuel in the combustion system.

Implementations can optionally include one or more of the following features. Dissociating the biomass waste under the thermochemical reaction can include producing carbon in addition to oxygenated carbon; and reacting the carbon with an oxygen donor in the presence of the waste heat to generate additional oxygenated carbon. Dissociating the biomass waste under the thermochemical reaction can include producing hydrocarbon and alcohol in addition to oxygenated carbon; and reacting the hydrocarbon and alcohol with an oxygen donor in the presence of the waste heat to generate additional oxygenated carbon. Combusting the oxygenated carbon in the charge combustion system can include providing multiple layers of an oxidant and the fuel mixture in a combustion zone of the combustion system. The method can include controlling timing or a duration of fuel injection using adaptive control. Also, the method can include controlling fuel delivery pressure in the charge combustion system. The combustion system can include a stratified-charge combustion system.

Yet in another aspect, a method of recycling carbon to produce an oxygenated fuel that includes oxygenated carbon and hydrogen can include harvesting carbon dioxide emitted from an industrial process. Biomass waste is dissociated under an anaerobic process to produce the carbon monoxide and hydrogen for the oxygenated fuel along with one or more carbon donors. Thermochemically shifted carbon monoxide and additional hydrogen are generated for the oxygenated fuel by reacting the harvested carbon dioxide with the biomass waste produced one or more carbon donors. The oxygenated fuel is combusted in a combustion system.

Implementations can optionally include one or more of the following features. The one or more carbon donors can include at least one of hydrocarbon and alcohol. Dissociating the biomass waste under the anaerobic process can include applying waste heat recovered from an external heat source. Generating the thermochemically shifted carbon monoxide can include applying waste heat recovered from an external heat source.

Yet in another aspect, a method of recycling carbon to produce a renewable fuel can include harvesting carbon dioxide emitted from an industrial process. Biomass waste is dissociated under an anaerobic reaction to produce hydrogen. The harvested carbon dioxide is reacted with the biomass waste produced hydrogen under pressure and heat to generate a renewable source of energy. The heat used in reacting the harvested carbon dioxide with the biomass waste produced hydrogen can include waste heat recovered from an external heat source. The combustion system can include a stratified-charge combustion system.

The subject matter described in this specification potentially can provide one or more of the following advantages. By providing oxygenated fuel before the combustion chamber, the described techniques can increase fuel efficiency by providing more complete combustion events. Also, the described techniques can act to prevent engine damages caused by the normally incomplete combustion process and degrading heat transfers associated with homogeneous charge combustion.

In addition, the described techniques and system can reduce or eliminate production of carbon dioxide, hydrocarbons, particulates, and oxides of nitrogen as described below:

A) Reducing fuel consumption: Carbon dioxide and hydrocarbon emissions can be reduced or eliminated in accordance with thermal and corresponding fuel-efficiency improvements;

B) Conversion of fuel-sourced carbon to an oxygenated fuel constituents such as carbon monoxide eliminates hydrocarbon particulate emissions; and C) Peak-combustion temperatures that cause formation of oxides of nitrogen can be eliminated by combustion of hydrogen-characterized fuel mixtures within surplus air according to an adaptive algorithm for the relative timing of fuel injection and plasma ignition events with respect to combustion chamber geometry, fuel penetration pattern, piston speed, BMEP requirement, and electronic monitoring of each combustion chamber temperature.

BRIEF DESCRIPTION OF THE DRAWINGS

Like reference symbols and designations in the various drawings indicate like elements.

DETAILED DESCRIPTION

The ignition delay of conventional diesel fuel made of a mixture of large-molecules as liquid-fuel constituents includes the time to evaporate and crack these molecules and then penetrate enough additional hot air to ignite. Small gaseous molecules, such as hydrogen ($H_2$) and carbon monoxide (CO) have much less delay and eliminate particulate formation. The time to complete combustion of any fuel is a function of the heat required to evaporate and crack the fuel, availability of the oxidant, heat released by combustion, and degree to which the heat release is conserved. In order to equalize kinetic energy in a population of mixed mass molecules, small molecules have much higher velocities than large molecules. Small molecules like hydrogen travel faster, traverse greater distances, collide more often, and diffuse more rapidly than larger molecules at the same temperature. Hydrogen burns in a much wider range of air-fuel ratios than most hydrocarbons. This along with the higher heat release as hydrogen oxidizes is why hydrogen burns 7 to 10 times faster than hydrocarbon fuels.

Techniques, structures, apparatus and materials are disclosed for generating oxygenated fuel for use in an engine to increase fuel efficiency by providing the oxygenated fuel before the combustion chamber to achieve a more complete combustion of the fuel. In addition, the process of providing the oxygenated fuel can prevent damages to the engine cause by the incomplete combustion process.

Oxygenation of Carbon-Donor

Figure 1:
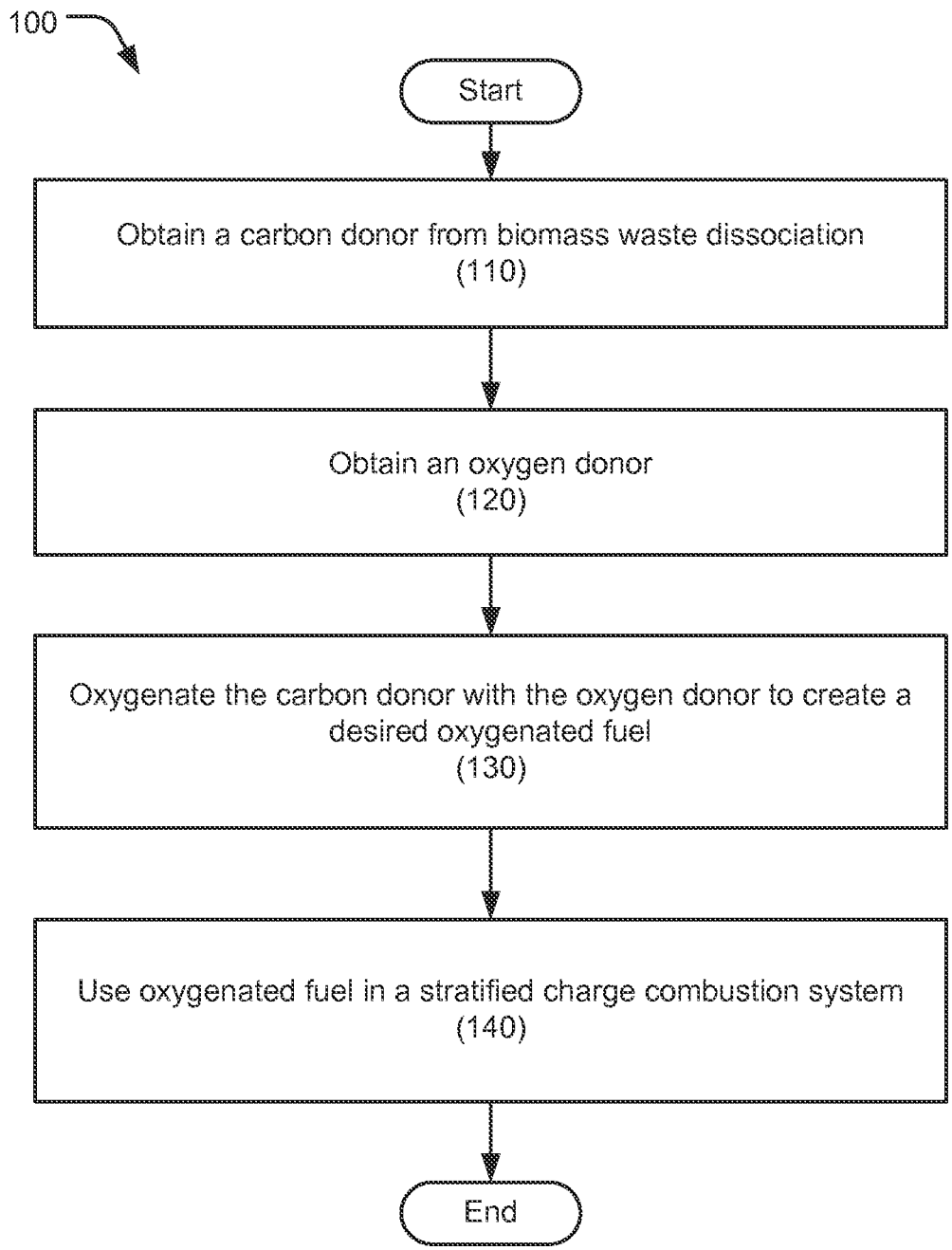
FIG. 1 is a process flow diagram of an exemplary process for generating oxygenated fuel from biomass waste and industrial waste.

FIG. 1 is a process flow diagram of an exemplary process 100 for generating oxygenated fuel from substances that include hydrogen and carbon such as biomass waste and industrial waste. A system (e.g., system 300 below) obtains a carbon donor, such as carbon, hydrocarbon or alcohol from biomass dissociation (110). Copending U.S. patent application Ser. No. 13/027,068 filed Feb. 14, 2011, now U.S. Pat. No. 8,318,997, and entitled "CARBON-BASED DURABLE GOODS AND RENEWABLE FUEL FROM BIOMASS WASTE DISSOCIATION" describes the techniques and systems for biomass waste dissociation, the entire contents of which are incorporated by reference. Briefly, Equation 1 below shows an exemplary general process for biomass waste dissociation to produce a carbon such as the hydrocarbon methane.

$$C_xH_yO_z + \text{HEAT} \rightarrow CH_4 + H_2 + CO_2 + CO \qquad \text{Equation 1}$$

Using the process described in Equation 1, virtually any organic material can be converted in large part to hydrocarbon fuel, such as methane (CH4) for distribution and storage in the existing natural gas infrastructure. Equation 2 below illustrates a general summary of overall reactions of an embodiment for production of methane from typical biomass wastes such as glucose, lignin, and cellulosic feedstocks.

$$C_6H_{12}O_6 + \text{HEAT} \rightarrow 3CH_4 + 3CO_2 \qquad \text{Equation 2}$$

In some implementations, the biomass dissociation reaction can produce alcohols, such as methanol as a readily storable and transportable liquid fuel and chemical precursor. Methanol or "wood alcohol" can be extracted by heating lignocellulosic wastes through partial combustion or by anaerobic heating processes. Equations 3 and 4 summarize the output of methanol that can be achieved by selection of different anaerobic operating temperatures, pressures, and catalysts.

$$C_6H_{12}O_6 + HEAT \rightarrow 6CO + 6H_2 \qquad \text{Equation 3}$$

$$6CO + 6H_2 \rightarrow 3CH_3OH + 3CO \qquad \text{Equation 4}$$

The system also obtains an oxygen donor to oxygenate the carbon donor (120). The system causes the carbon donor to react with the oxygen donor to oxygenate the carbon donor to obtain the desired oxygenated fuel (130). The reaction is endothermic, in which heat used in the oxygenation reaction can be harvested from waste heat of an engine exhaust or cooling system. Also, heat used in the reaction can be obtained from a renewable source of energy, such as wind and solar power generators. Moreover, the equipments for the wind and solar power generator can be produced using carbon-based materials, which were created from the carbon extracted from the biomass dissociation.

The oxygenated fuel can be used in a stratified charge-combustion system, such as a diesel or gasoline engine (140) that has been converted to such operation. In some implementations, the combustion system can include a stratified charge combustion system. The oxygenated fuel can increase the fuel efficiency by promoting more complete combustion and also prevent engine damages caused by normally incomplete combustion process.

For example, an industrial operation or refining operation can produce pressurized carbon dioxide, carbon monoxide and/or hydrogen by partial oxidation of a carbon donor or by reaction of a carbon donor with steam as generally shown in Equations 5-8.

$$2C + 1.5O_2 \rightarrow CO + CO_2 \qquad \text{Equation 5}$$

$$CH_4 + H_2O + HEAT \rightarrow CO + 3H_2 \qquad \text{Equation 6}$$

$$C_xH_y + 0.5xO_2 \rightarrow xCO + 0.5yH_2 \qquad \text{Equation 7}$$

$$CH_4 + 0.5O_2 \rightarrow CO + 2H_2 + HEAT_2 \qquad \text{Equation 8}$$

Equation 7 summarizes partial oxidation of a hydrocarbon compound, which can be beneficial for producing hydrogen along with oxygenated carbon. Equation 8 summarizes the partial oxidation of methane. The oxygen utilized in the processes of Equations 7 or 8 may be supplied by air, air filtration, air separation processes, or by electrolysis of a compound such as water that separates oxygen from another substance such as hydrogen.

Extensive studies of the combustion rates at various pressures show that carbon monoxide combusts at a much slower rate than hydrogen. For example, see Hongyan Sun, S. I. Yang, G. Jomaas, and C. K. Law; *High-pressure laminar flame speeds and kinetic modeling of carbon monoxide/hydrogen combustion*, Proceedings of the Combustion Institute 31 (2007) 439-446. However, the described techniques and systems provides for much faster combustion of carbon monoxide or mixtures of carbon monoxide including other relatively slow burning hydrocarbon constituents or with much faster burning hydrogen by minimizing or preventing oxides of nitrogen from forming, for example.

Previous approaches for gaining an advantage by electrolysis of water using "off-peak" renewable electricity or grid-delivered electricity from mixed power sources or by electrolysis on board a vehicle including arrangements for regenerative braking to produce electricity and or heat to dissociate a compound such as water have wasted the oxygen or added oxygen to a fuel cell or an engine. The present invention derives a much greater benefit by oxygenation of carbon to produce a fuel or fuel mixture with much more rapid combustion characteristics and results. An important benefit of the "oxygenation" of all the carbon in the original fuel is the assurance that all of the carbon will be rapidly combusted without particulate production in the combustion process (e.g., stratified-charge combustion) that is enabled by Fuel injector or multi-fuel injector technology.

For the reaction of Equation 9 below, coal wastes, sawdust, refinery wastes, oil tar, grain processing dust, forest-fire debris, particle dust from manufacturing processes that utilize carbon compounds are suitable sources for production of oxygenated carbon.

$$C + H_2O + HEAT \rightarrow CO + H_2 \qquad \text{Equation 9}$$

Figure 2:
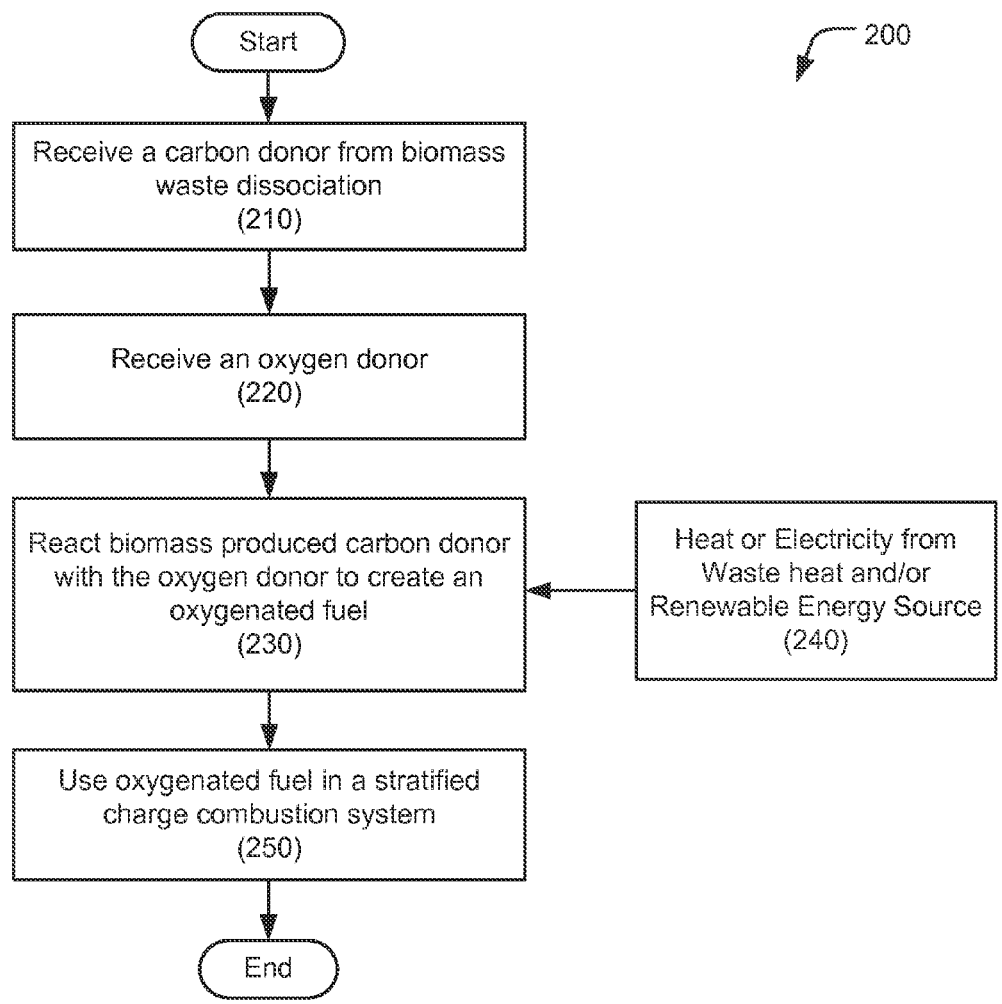
FIG. 2 is a process flow diagram of an exemplary process for selectively producing oxygenated fuel in a multi-fuel environment.

FIG. 2 is a process flow diagram of an exemplary process 200 for selectively producing oxygenated fuel in a multi-fuel environment. A system (e.g., system 300 below) can receive a carbon donor from biomass dissociation (210). The process for biomass dissociation to obtain various carbon donors is described above with respect to FIG. 1. The system also receives an oxygen donor in the form of oxygen, steam, water, etc. (220).

The system causes the carbon donor to react with the oxygen donor (e.g., oxygenation) in an exothermic or endothermic reaction (230). For multi-fuel applications, depending on the chemical nature of the fuel stored in a tank, the system can include one or more heat exchangers that selectively apply varying degrees of heat and pressure to produces corresponding varieties of hydrogen-characterized fuels for improving the operation of an engine (240). For example, wet methanol can be vaporized and dissociated by addition of heat to produce hydrogen and carbon monoxide as shown in Equation 10. Equation 11 shows endothermic reforming of inexpensive wet ethanol or with addition of an oxygen donor such as water:

$$2CH_3OH + H_2O + HEAT \rightarrow 5H_2 + CO + CO_2 \qquad \text{Equation 10}$$

$$C_2H_5OH + H_2O + HEAT \rightarrow H_2 + 2CO \qquad \text{Equation 11}$$

When compounds such as cellulose and fuel alcohols, which contain oxygen, are dissociated by anaerobic decomposition, the general process as illustrated with ethanol feedstock is shown regarding Equation 12.

$$C_2H_5OH + HEAT \rightarrow C + CO + 3H_2 \qquad \text{Equation 12}$$

Hydrogen and carbon monoxide of desirable quality to be directly utilized in most of the world's existing engines is released by the dissociation process generalized by Equations 5-12, for example. Hydrogen characterized fuels produced according to such reactions can be used to fuel an engine or used as a low cost fuel for customers' heat engines including piston and gas turbine types. In such applications, a fuel injector or a multi-fuel injector described in U.S. Pat. No. 6,756,140 entitled "Energy Conversion System," the entire contents of which are incorporated by reference, can be used to improve power production, clean the air, and extend engine life while using such hydrogen-characterized fuel.

The selectively generated oxygenated fuel can be used in a combustion system, such as a converted gasoline or diesel engine (250). In some implementations, the combustion system can include a stratified combustion system.

Figure 3A:
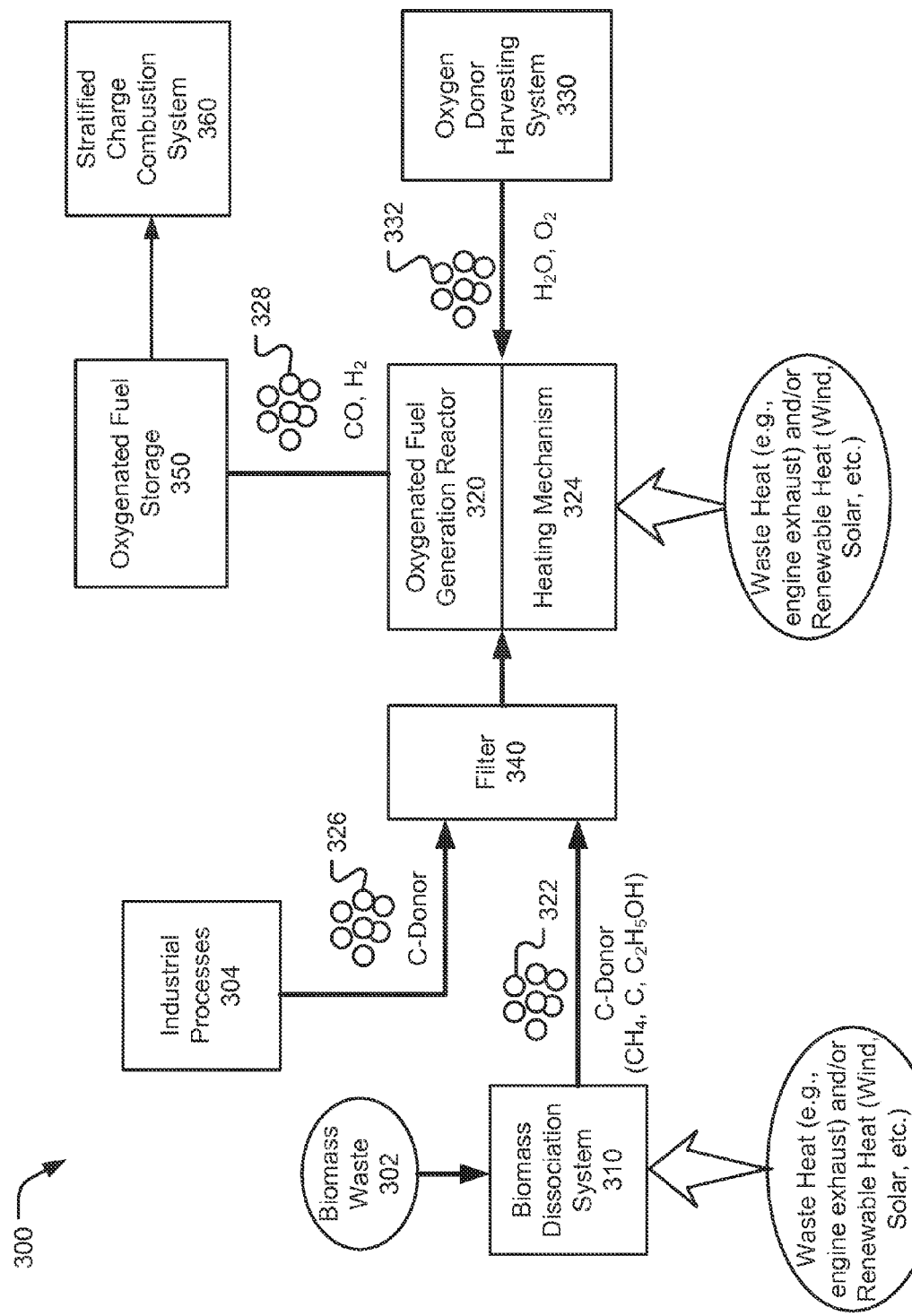
FIG. 3A is a block diagram showing an exemplary system for generating oxygenated fuel from biomass waste.

FIG. 3A is a block diagram showing an exemplary system 300 for generating oxygenated fuel from biomass waste. The system 300 includes a biomass dissociation system 310 that receives biomass waste 302 to be dissociated into carbon-donors 322, such as carbon, hydrocarbons, alcohols, ammonia and hydrogen using a thermochemical regenerative process. The heat used to dissociate the biomass waste 302 can include waste heat from sources such as fuel cell and/or engine exhausts, engine cooling system etc. that otherwise would be released to the environment. Also, one or more of renewable energy sources, such as wind, solar, etc. can be used to generate the heat.

The carbon-donors 322 received from the biomass dissociation system 310 are forwarded to an oxygenated-fuel generating reactor 320, which includes a heat transfer system for heating or cooling mechanism 324. The oxygenated-fuel generating reactor 320 can also receive additional or different carbon donors, such as $CO_2$ 326 harvested from industrial processes (e.g., exhaust gases from fossil fuel combustion or air) 304. In addition, the oxygenated-fuel generating reactor 320 receives oxygen-donors 332 from an oxygen-donor harvesting system 330.

The oxygenated-fuel generating reactor 320 causes the received carbon-donors 322 and 326 to react with the harvested oxygen-donors 332 to generate an oxygenated fuel mixture that can include carbon monoxide and hydrogen. The reactor 320 with the heating mechanism 324 performs heat transfers and operations to accomplish thermochemical regeneration for efficient reaction. The system 300 can also include a controller (not shown) that adaptively adjusts the coordination of pumps (not shown), valves (not shown), and heating operations to optimize specific and overall the processes. Methane can be delivered by a pressure adjusting pump (not shown) from the biomass dissociation system 310 to the heating mechanism 324 where it is heated to approach the decomposition temperature by countercurrent heat exchange from hydrogen and/or carbon monoxide exiting the oxygenated fuel generation reactor 320.

Hot coolant and the exhaust from an engine can successively supply waste heat to one or more counter current heat exchangers (e.g., part of the heating mechanism 324) and the reactor 320 in which a precursor such as methane, naphtha, ethanol, or methanol and/or other products from fresh or fossil biomass which may be delivered by a suitable transport system including a pipeline and reacted with an oxygen donor 332, such as water and/or oxygen to produce hydrogen and carbon monoxide according to Equation 6.

The generated oxygenated-fuel or mixture 328 can be stored at storage and/or transport system 350. Also, the oxygenated-fuel or mixture 328 can be sent to a combustion system 360, such as a converted diesel engine. In some implementation, the combustion system can include a stratified charge combustion system. The generated oxygenated-fuel or mixture 328 can include small gaseous molecules, such as hydrogen ($H_2$) and carbon monoxide (CO), which have much less delay and eliminate particulate formation. As described above, small molecules like hydrogen travel faster, traverse greater distances, collide more often, and diffuse more rapidly than larger molecules at the same temperature. Hydrogen burns in a much wider range of air-fuel ratios than most hydrocarbons. This along with the higher heat release as hydrogen oxidizes is why hydrogen burns 7 to 10 times faster than hydrocarbon fuels.

Equation 6 above, which is reproduced below, shows that the amount of water produced by combustion of a hydrocarbon, such as methane, is two or three times as much water as needed to reform methane into more desirable hydrogen-characterized fuel. Also, Equations 6 (reproduce from above) and 13 below show the advantage of reforming a hydrocarbon such as methane and burning the resultant fuel species ($H_2$ and CO) of Equation 6 to produce more expansion gases in the power stroke of the combustion chamber along with producing more water for reforming reactions in a reactor (e.g., reactor 320).

$$CH_4 + H_2O + HEAT \rightarrow CO + 3H_2 \qquad \text{Equation 6}$$

$$3H_2 + CO + 2O_2 \rightarrow 3H_2O + CO_2 \qquad \text{Equation 13}$$

In other words, reforming methane with water to make and combust producer gas (hydrogen and carbon monoxide) provides more combustion energy and about three-times as much product water as needed for the endothermic reformation of methane in the reactor (e.g., oxygenated fuel generation reactor reactor 320). Thus, along with water condensed in a heating mechanism (e.g., heat exchanger 324) of the reactor ample water can be collected by a vehicle or stationery application of the techniques and system for generating oxygenated fuel 328. This is a very important advantage for minimizing curb weight because most of the weight of water used in the oxygenated fuel generating reactor 320 is gained by combustion oxygen from the air with hydrogen or hydrogen-characterized fuel in the engine. Thus, each gram of hydrogen can combine with eight grams of atmospheric oxygen to provide nine grams of collectable water from the exhaust of engine.

In some implementations, power for propulsion and manufacturing operations can be provided by one or more heat engines that utilize thermochemical regeneration principles to increase thermal efficiency. For example, heat released by engine combustion can be harvested and recycled using heat exchangers. In addition, steam generated by burning of the oxygenated fuel can be used in the reaction of Equation 6 to oxygenate the carbon donors 326 and 322. Thus, both waste heat and water byproduct (e.g., steam) of an engine or reactor that combust the oxygenated-fuel 328 can be recycled to enhance an anaerobic (e.g., thermochemical or electroysis of water) reaction.

The system 300 can also include a filtration/precipitation system 340 to filter the carbon-donors, such as methane or other hydrocarbons and fuel constituents to remove sulfurous substances such as odorant, sulfides, and metal organics. When the presence of an odorant is desired, the appropriate odorant can be added, after the filtration, from concentrated sources that meter the desired amount into the carbon-donors. For example, semiconductor detectors of fluid leakage can be implemented at far lower concentrations than can often be detected by smelling an odorant.

Figure 3B:
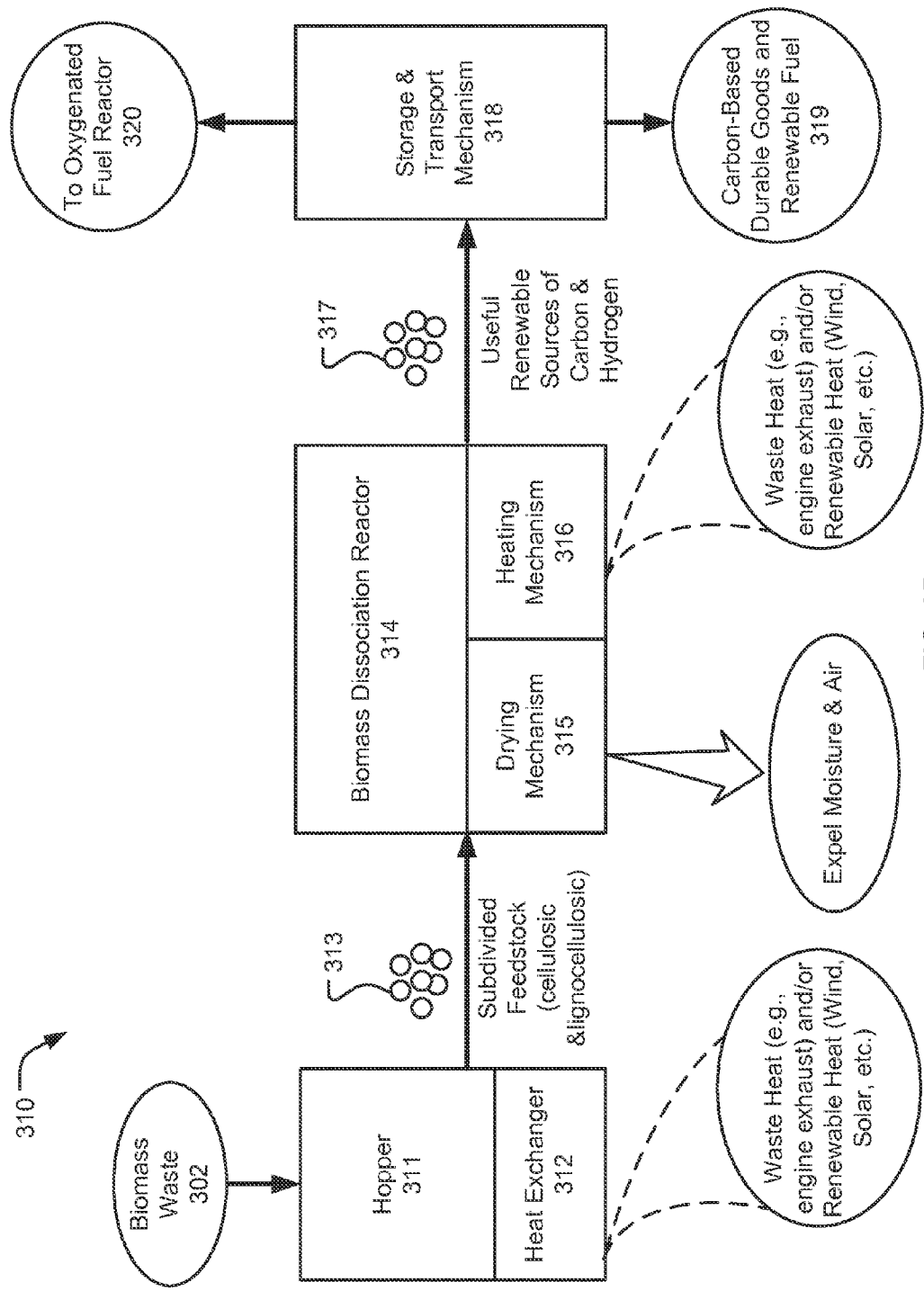
FIG. 3B is a block diagram showing an exemplary system for dissociating biomass waste into hydrogen and carbon carrying intermediaries.

FIG. 3B is a block diagram showing an exemplary system 310 for dissociating biomass waste into hydrogen and carbon carrying intermediaries. The system 310 includes a biomass waste intake component, such as a hopper 311 that receives the biomass waste 302 in raw form and breaks down (e.g., chips, chops, grinds, etc.) the raw material into subdivided feedstock, such as various cellulosic and lignocellulosic materials. The hopper 311 can include a heating mechanism, such as a heat exchanger 312 to pre-heat the subdivided feedstock. The heat exchanger can recapture and recycle waste heat from an external heat source (e.g., engine exhaust and/or renewable heat, such as wind, solar, etc.) or from biomass dissociation reactor 314 itself.

The subdivided (and in some implementations, pre-heated) feedstock 313 is forwarded to a biomass dissociation reactor 314 to dissociate the biomass waste feedstock into useful renewable sources of carbon and hydrogen, such as various hydrocarbons, alcohols, ammonia, and oxides of carbon. The reactor can include a drying mechanism 315 to expel moisture and air from the feedstock. The drying mechanism 315 can include an extruding device to physically 'squeeze out' the moisture and air from the feedstock. Examples of the extruding device include a helical screw conveyer and a ram piston conveyer. Also, the drying mechanism 315 can include one or more heating mechanisms, such as heat exchangers that capture heat generated by the reactor 314 and recycle the captured heat to dry the feedstock. The heat exchangers can also recapture and recycle waste heat from an external heat source (e.g., engine exhaust and/or renewable heat, such as wind, solar, etc.)

The reactor 314 can also include a heating mechanism 316 for generating adequate heat used in an anaerobic reaction to dissociate the biomass waste feedstock into the useful renewable sources of carbon and hydrogen 317, such as hydrocarbons, alcohols, ammonia and oxides of carbon. The generated useful renewable sources of carbon and hydrogen 317 can be forwarded to a storage and/or transport mechanism 318 to be used by the oxygenated fuel generation reactor 320 and in additional reactions to generate renewable fuel and/or carbon-based durable goods 319 as described in the copending U.S. patent application Ser. No. 13/027,068 filed Feb. 14, 2011, now U.S. Pat. No. 8,318,997, entitled "Carbon-Based Durable Goods and Renewable Fuel from Biomass Waste Dissociation," the entire contents of which is incorporated by reference. Moreover, the storage and/or transport mechanism 318 allows for efficient transport of the useful renewable sources of carbon and hydrogen 317 to remote locations for further processing.

The biomass dissociation reactor 314 can be configured to increase the thermal efficiency of the biomass waste conversion process while reducing or eliminating carbon dioxide formation. For example, the biomass dissociation reactor 314 can include mechanisms to perform various countercurrent drying (e.g., recycling heat) and elimination of air, moisture, and other oxygen donors prior to extraction of carbon, hydrocarbons such as methane, and/or hydrogen.

The described techniques and system allow utilization of biomass alcohols from much lower-cost production methods by allowing substantial water to remain mixed with the alcohol as it is produced by destructive distillation, synthesis of carbon monoxide and hydrogen and/or by fermentation and distillation. This enables more favorable energy economics as less energy and capital equipment is required to produce wet alcohol than dry alcohol. Further it facilitates the utilization of waste heat from an engine to endothermically create hydrogen and carbon monoxide fuel derivatives and to release up to 25% more combustion energy than the feedstock of dry alcohol. Additional benefits are derived from the faster and cleaner burning characteristics provided by hydrogen. By utilization of Fuel injector or multi-fuel injector to meter and ignite such hydrogen-characterized derivative fuel as a stratified charge in unthrottled air, overall fuel efficiency improvements of more than 40% compared to homogeneous charge combustion of dry alcohol(s) are achieved.

Thermochemically Shifted Carbon Monoxide

Figure 4:
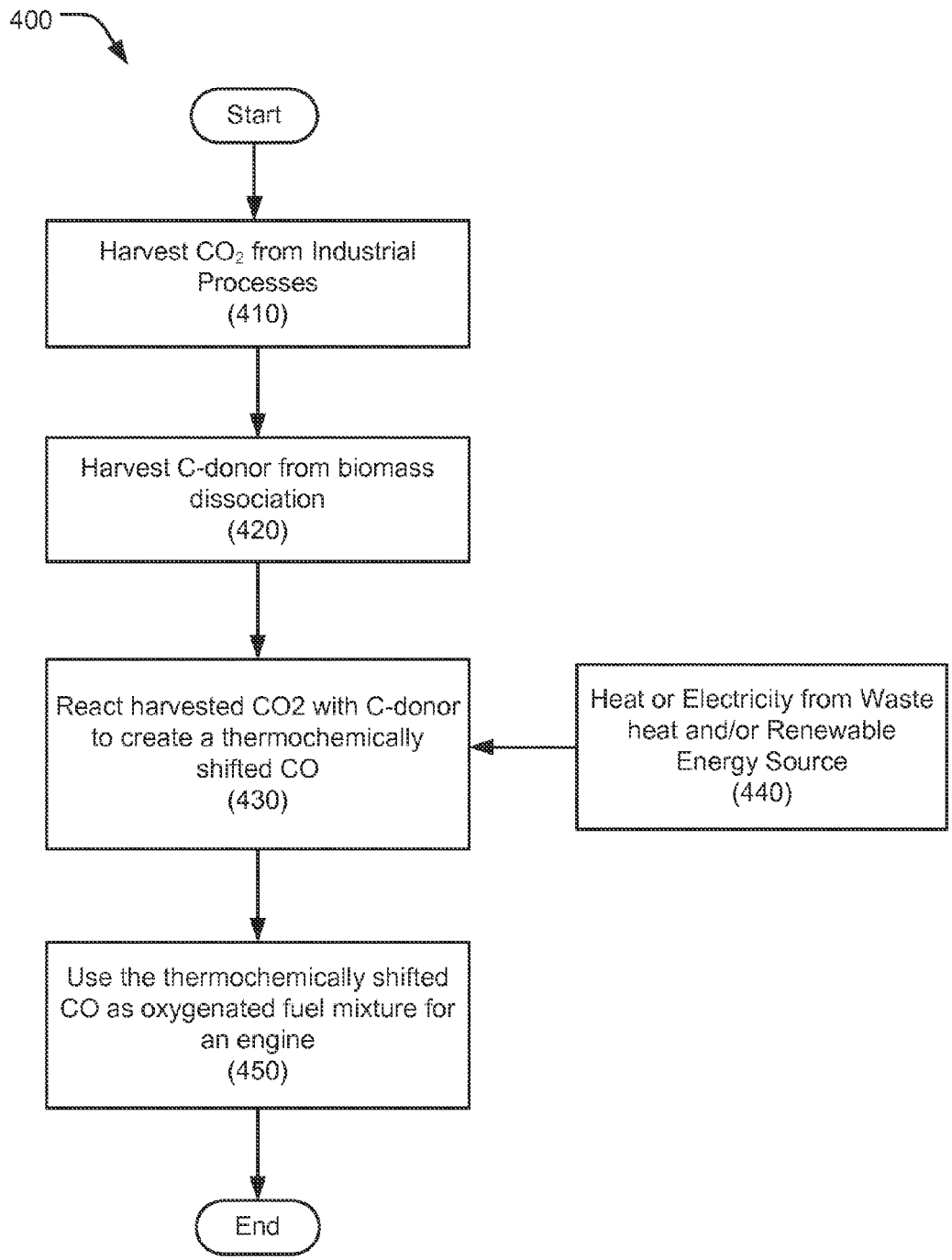
FIG. 4 is a process flow diagram showing an exemplary process for generating thermochemically shifted carbon monoxide for use as oxygenated fuel.

In another aspect, when substantial sources of carbon dioxide are available such as from the stack gases of fossil fueled power plants, such carbon dioxide can be harvested, separated, and purified as disclosed in the U.S. Pat. No. 6,984,305, the entire contents of which are incorporated by reference. FIG. 4 is a process flow diagram showing an exemplary process 400 for generating thermochemically shifted carbon monoxide for use as oxygenated fuel. A system (e.g., system 500) harvests $CO_2$ from industrial processes as described above (410). The system also harvests a carbon-donor (e.g., from biomass dissociation) (420). The industrial process harvested $CO_2$ can be repurposed and recycled as a source of thermochemically shifted CO by reacting the fossil produced carbon dioxide with a renewable carbon donor (e.g., from biomass dissociation) as shown in Equation 14.

$$CO_2 + C \rightarrow CO \qquad \text{Equation 14}$$

Ultimately, such $CO_2$ and carbon wastes are heated sufficiently in an anaerobic environment to release desirable gases, carbon, and solid residues such as mineral oxides and other compounds (430). The heat used in the reaction to generate the thermochemically shifted carbon monoxide can be obtained from waste heat of an engine exhaust or cooling system (440). Also, heat or energy from renewable resources, such as wind or solar energy generators can be used. As described with respect to FIG. 1 above, even the equipments for the renewable energy generation can be produced using carbon extracted from biomass dissociation.

The thermochemically shifted CO can be used as oxygenated fuel mixture in an engine (e.g., a combustion system), such as a stratified charge engine (450).

Figure 5:
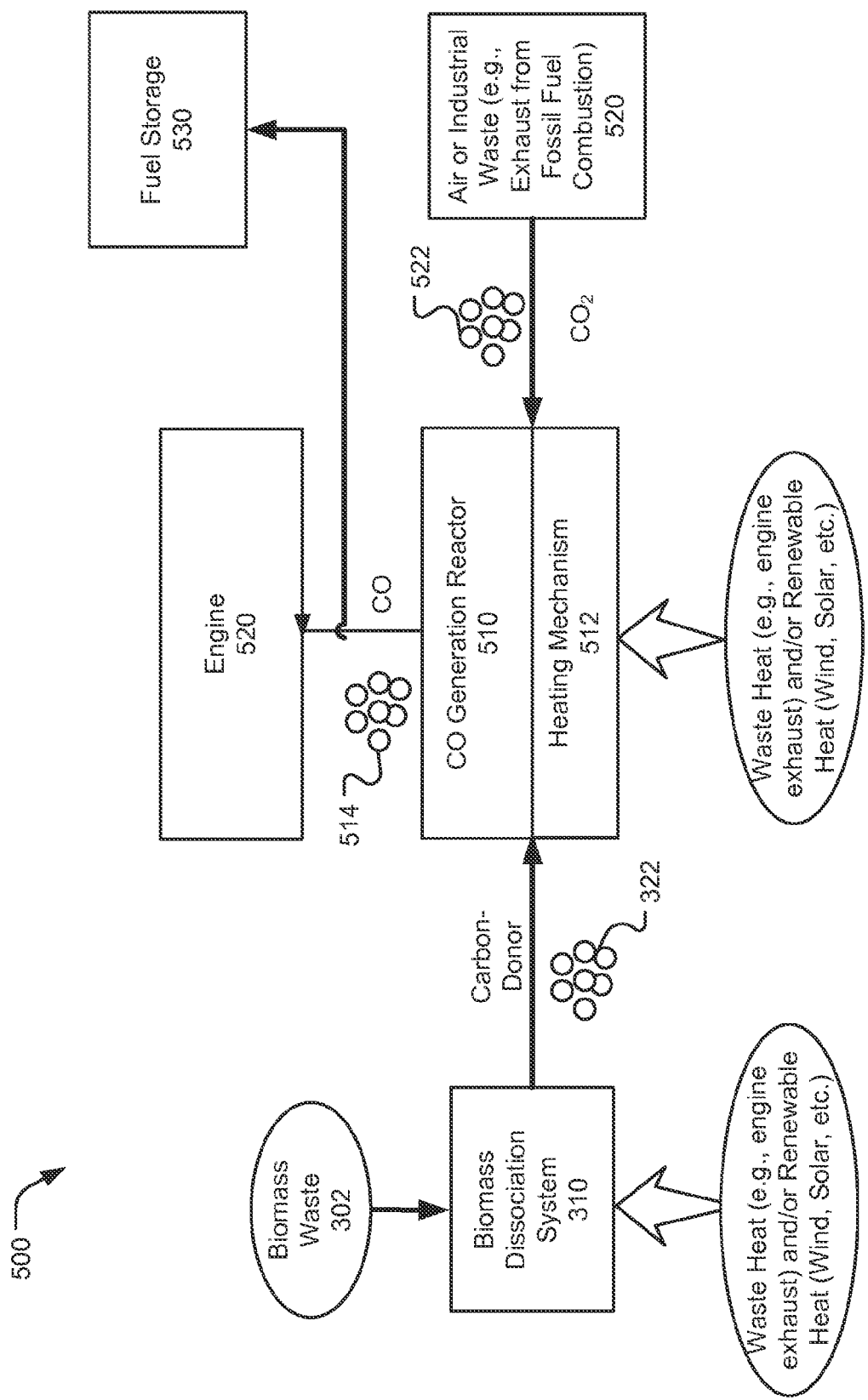
FIG. 5 is a block diagram of an exemplary system for generating renewable fuel from thermochemically shifted CO reacted with hydrogen from biomass waste dissociation.

FIG. 5 is a block diagram of an exemplary system 500 for generating renewable fuel from thermochemically shifted CO reacted with hydrogen from biomass waste dissociation. The system 500 includes a biomass dissociation system 310 that receives biomass waste 302 to be dissociated into carbon, hydrocarbons, alcohols, ammonia and hydrogen using a thermochemical regenerative process. The heat used to dissociate the biomass waste 302 can include waste heat from engine exhausts, engine cooling system etc. that otherwise would be released to the environment. Also, one or more of renewable energy sources, such as wind, solar, etc. can be used to generate the heat.

From the biomass dissociation system 310, carbon donor 322 (from dissociation of hydrocarbons, for example) is captured and forwarded to a carbon monoxide (CO) generating reactor 510, which includes a heating mechanism 512. The carbon donor 322 is reacted with $CO_2$ 522 harvested from industrial processes (e.g., exhaust gases from fossil fuel combustion or air) 520. The CO generating reactor 510 can cause the carbon donor 322 to react with the harvested $CO_2$ 522 to generate thermochemically shifted CO 514.

The thermochemically shifted CO 514 is forwarded to an engine 520 and used as oxygenated fuel. Also, the thermochemically shifted CO 514 is storable and transportable at a storage container 530.

In some implementations, an electrolyzer can be included to supply oxygen to pressurize or be added to pressurized constituents in a heat exchanger to oxidize a portion of a quantity of feedstock and or provide partially oxidize such fuel constituents and supplement the heat available by heat exchanges from sources such as solar, engine jacket heat, and exhaust heat. Moreover, the heat from reactions within the oxygenated fuel generating reactor 320 or thermochemically shifted CO generating reactor 510 can be recycled as part of the heat used for endothermic processes and or exothermic reactions described above.

Separation of CO and H2 and Storage

Hydrogen produced by the reaction of Equations 8-10 may be separated from carbon monoxide by a suitable separation system such as diffusion through a membrane in a separator (not shown) or by pressure swing adsorption or temperature swing adsorption is stored in an accumulator 30 which may be of the type disclosed in U.S. Pat. Nos. 6,446,597 and 6,503,584, the entire contents of which are incorporated by reference. Carbon monoxide can be stored in another accumulator and may be used as fuel in an engine 520 or as a fuel source to fuel injector and spark igniter to provide supplemental heat for accelerating thermochemical regeneration in the reactors 320 and 510. Such separation facilitates the utilization of relatively pure hydrogen independent of CO.

Tangible and Useful Applications: Fuel Injector or Multi-fuel Injector for Efficient Engine Operation The described techniques for generating oxygenated fuel (e.g., CO or CO+$H_2$) can be applied to an engine that implements a Fuel injector or multi-fuel injector that may be similar to the integrated fuel injection and spark ignition devices disclosed in U.S. Pat. Nos. 3,830,204; 4,066,046; 5,343,699; 6,155,212; 6,446,597; 6,756,140; or 7,628,137, the entire contents of these patents are incorporated by reference. In addition, multi-fuel injector technology can be implemented to provide a process of multi-fuel presentation for ignition and combustion that may include carbon monoxide, mixtures of carbon monoxide and other fuel constituents, or carbon monoxide and non-fuel substances or in the alternative may include other fuel selections such as diesel fuel, gasoline, propane, fuel alcohols, wet fuel alcohols, wet fuel alcohols with carbon donor additions, or hydrogen provides for much more rapid completion of combustion processes than possible by previous approaches. Multiple layers of oxidant and fuel can be provided in the combustion zone of a fuel combustion system. Positive ignition of multiple direct fuel injections to form pancaked layers of fuel separated by air or another suitable oxidant such as oxygen in different zones can provide much more rapid completion of combustion processes. Multi-fuel injection can be controlled using a controller that provides a drive signal for a piezolectric or electromagnetic or hydraulic or pneumatic valve operation to deliver fuel to the combustion chamber of the engine.

The controller may subsequently provide a drive signal to ignite one or more layers of fuel as they enter the combustion chamber, during the time fuel is entering the combustion chamber or after fuel has entered the combustion chamber. Such ignition may be by a spark or by bursts of more than one sparks or by continuous application of spark plasma and may be applied with or without catalytic fuel modification within a system or with or without catalytic ignition at the location of fuel entry into the combustion chamber. The controller may receive information about the pressure and or the temperature resulting from the fuel introduction and or ignition and or combustion events in the combustion chamber by wireless communication or by instrumentation lead. The controller can control the pressure of fuel delivery through a conduit to the combustion chamber and may also receive flow rate information by wireless communication and or by the lead or a similar method of communication.

In addition, adaptive control may be provided for the timing and duration of each fuel injection, and the timing and duration of each ignition, and of the fuel delivery pressure by the controller to produce constant rpm, a desired acceleration or deceleration, maximum fuel economy, or minimum oxides of nitrogen, or certain operating temperature(s) of one or more engine components such as pistons, valves, a cylinder wall, or the rings of the pistons.

Consequently, higher torque can be developed per calorie or BTU (British Thermal Unit) for greater fuel efficiency and to prevent oxides of nitrogen from being formed. Higher torque per BTU is provided by timing the ignition of more rapid combustion processes closer to, at, or after top dead center (TDC). Thus the resulting higher surface to volume ratio provides for much more rapid heating of air between and around the pancaked layers of combusting fuel than possible with previous technologies.

Oxides of nitrogen are greatly reduced or prevented by igniting locally fuel-rich mixtures that propagate combustion into locally air-rich mixtures to limit peak combustion temperatures of such zones to 2200° C. (4000° F.). Additional benefits are provided by the more rapid completion of multiple stratified charge combustion for preventing formation of oxides of nitrogen by reducing the time for oxides of nitrogen to be formed and reducing or eliminating quench preservation of any oxides of nitrogen that may be formed.

Another important benefit is that hydrogen may be co-produced by regenerative braking or application of off peak electricity along with subsequent oxygenation of carbon. Hydrogen combusts 7-10 times faster than fossil fuels such as methane, octane, propane, ethane and diesel fuel constituents. In applications on engines operating at relatively high frequency such as 3,000 to 15,000 rpm (revolutions per minute) very little time is available for completion of combustion and hydrogen may be used at times that an expedited combustion process is needed. Multiple stratified coniform fuel charges or flatter stacks of "fuel pancakes" with air or air-rich or oxygen or oxygen rich layers between such multiple stratified coniform fuel charges or flatter stacks of fuel pancakes expedites the completion of combustion of all fuel selections but operation of high speed engines with hydrogen is particularly beneficial. At relatively low piston speeds, slower burning fuels such as methane, ethane, propane, octane, gasoline, or fuel alcohols may be delivered through a conduit. At higher piston speeds, faster burning fuels may be added to supplement or replace such slower burning fuels. Illustratively, hydrogen or mixtures of hydrogen and carbon monoxide may be delivered by a conduit for adding to or replacing slower burning fuel selections.

The power, as may be measured as horse power "HP" developed by an engine is equal to the product of brake mean effective pressure "BMEP" or "P", the length of stroke of the piston for providing torque, and the frequency or number of cycles of operation per unit of time "N"

$$HP = PLAN \qquad \text{Equation 15}$$

As summarized in Equation 15, more power can produced because P is increased and more rapid completion of combustion enables N to also be increased for additional power or more torque by gear-reduction when needed. In addition, more heat can be delivered to the combustion chamber by the faster burning oxygenated carbon and hydrogen than the original fuel would release upon combustion.

Computer-aided controls and components provide direct-injection and spark-ignition of traditional and alternative fuels in internal combustion engines can provide important improvements to energy-conversion efficiency with hydrocarbon fuels and enables utilization of lower cost renewable fuels including hydrogen, methane, and oxygenated carbon regardless of octane or cetane rating. Fuel or multi-fuel injection can provide full rated power production with gaseous fuels such as natural gas, renewable methane, or hydrogen that require far greater fuel flow rates to provide the same heating value as Diesel fuel. Adaptive electronic controls monitor crankshaft acceleration, cylinder pressure, and piston speed for purposes of minimizing fuel use through all duty cycles including start-up, idle control, acceleration, transient operation, cruise, frequency matching, and full-power development. Each fuel injection and ignition event is monitored and adjusted to produce maximum torque within the selected duty cycle. The variables are timing of fuel injection, spark ignition, and amount of fuel injected.

Tangible and Useful Applications: Thermochemical Regeneration

Thermo chemical regeneration and/or regenerative braking energy can be utilized or combined in a Thermochemical Regeneration process to produce greater fuel values from hydrocarbon fuels and an oxygen donor such as methanol and or water. Heat recovered from the cooling and exhausts systems and/or regenerative braking produce hydrogen from hydrocarbon fuels or water and convert hydrocarbons and a suitable oxygen donor by endothermic steps including vaporization and formation of gaseous fuel species that yield greater energy upon combustion than the original hydrocarbon precursor fuel.

Tangible and Useful Applications: Efficient Improvements for Emissions Reduction As described above, the ignition delay of conventional diesel fuel made of a mixture of large-molecules as liquid-fuel constituents includes the time to evaporate and crack these molecules and then penetrate enough additional hot air to ignite. Small gaseous molecules (such as $H_2$ and CO) have much less delay and eliminate particulate formation. The time to complete combustion of any fuel is a function of the heat release, availability of the oxidant, and degree to which the heat released is conserved. In order to equalize kinetic energy in a population of mixed mass molecules, small molecules have much higher velocities than large molecules. Small molecules like hydrogen travel faster, traverse greater distances, collide more often, and diffuse more rapidly than larger molecules at the same temperature. Hydrogen burns in a much wider range of air-fuel ratios than most hydrocarbons. This along with the higher heat release as hydrogen oxidizes is why hydrogen burns 7 to 10 times faster than hydrocarbon fuels.

Increased BMEP for improving specific power rating: One way to improve BMEP is to prepare fuel constituents that burn more rapidly to enable pressure development during the power stroke for reduced backwork during the compression stroke. Reversible theoretical cycle efficiency is not influenced by pressure, however practical cycle efficiency is greatly influenced by pressure because the greater the pressure the faster the combustion process and backwork and heat losses are reduced during compression in nonadiabatic positive-displacement engines.

Reaction rates for CxHy are generally much slower than for smaller $H_2$ and CO molecules in which the surface to volume ratio of the small molecules are larger than for larger hydrocarbons. The first step of reacting carbon in a hydrocarbon is an endothermic reaction in which heat is required to release the hydrogen from the carbon in order for the carbon to be oxidized. Subsequently, the greater portion of heat released by hydrocarbon-sourced carbon combustion is from the step of carbon monoxide being oxidized to form carbon dioxide a shown in Equations 16-17:

$$C+0.5O_2 \rightarrow CO-47{,}517 \text{ BTUs/Mole} \qquad \text{Equation 16}$$

$$CO+0.5O_2 \rightarrow CO_2-121{,}666 \text{ BTUs/Mole} \qquad \text{Equation 17}$$

The described techniques can provide heat transfer from the cooling fluid and exhaust system for endothermic reactions to prepare free hydrogen and fully oxygenated carbon as carbon monoxide. This can provide improved system efficiency, reduces maintenance and extends engine life because less heat is transferred from these fast burning fuels to the piston, rings, cylinder walls and valve assemblies.

In addition to hydrogen produced by regenerative braking, engine cooling jacket temperature is adequate to provide significant heat addition for endothermic thermochemical regeneration process steps. Exhaust gas temperatures are substantially adequate to add heat at higher temperatures to accomplish completion of endothermic reactions with hydrocarbon feed stocks including liquid and lower-cost gaseous fuels such as landfill methane as shown in above described Equations 6, 13 (reproduced below) and Equation 18:

$$CH_4+H_2O+HEAT_8 \rightarrow CO+3H_2 \qquad \text{Equation 6}$$

$$CO+3H_2+2O_2 \rightarrow CO_2+3H_2O+HEAT_9 \qquad \text{Equation 13}$$

$$CH_4+2O_2 \rightarrow CO_2+2H_2O+HEAT_{10} \qquad \text{Equation 18}$$

The heat of reaction at constant pressure of Equation 18 is −344,940 BTU/Mole. In the combustion process shown in Equation 13, −103,968 BTU/Mole for 3 moles of Hydrogen=−311,904 BTU; and −121,666 BTU/Mole for combusting CO provide a total yield of −433,570 BTU. This is the lower heating value without any credit for the heat of condensation of 3 moles of water. Compared to Equation 18, Equation 13 yields −88,630 BTU more energy than burning the methane directly. Thus, about 25% more combustion energy is delivered for production of work. Thermochemical regeneration does not require the new fuel species to be used at elevated temperature and the new species can regeneratively transfer heat to the thermochemical process. The $Heat_8$ used to reform methane and water into oxygenated carbon and hydrogen may include heat transferred from the engine's cooling system and heat transferred from the engine's exhaust system and may further include heat contributed by partial oxidation of a carbon donor fuel.

Tangible and Useful Applications: Dissociation of H2-Dense Fuel Used as Solvent to Isolate Contaminants In some implementations, methanol and water solution produced from a reaction of biomass dissociation produced hydrogen with $CO_2$ harvested and repurposed from industrial processes may also serve as a solvent for soluble organics that are functional hydrogen and carbon donors. For example, a thermochemical regeneration may utilize waste heat from a renewable energy source, fuel cell or heat engine and the inexpensive "wet" liquid mixture or may contain soluble carbon or various organics that are depicted as "C" as shown in Equation 19.

$$CH_3OH+H_2O+C+HEAT \rightarrow 2CO+3H_2 \qquad \text{Equation 19}$$

The heat of reaction of methane at constant pressure of Equation 18 is −344,940 BTU/Mole. But for three moles of hydrogen it is 3(−103,968 BTU/Mole)=−311,904 BTU; and 2(−121,666 BTU/Mole)=−243,332 for combusting 2CO in Equation 19 for a total yield of −555,236 BTU. This is the lower heating value without any credit for the heat of condensation of 3 moles of water. Compared to Equation 18 (yielding −344,940), it yields −210,296 BTU more energy than burning the initial feedstock methane directly. Thus, about 60% more combustion energy is delivered for production of work by the engine. Thermochemical regeneration does not require the new fuel species to be used at elevated temperature and the new species can regeneratively transfer heat to the thermochemical process.

Suitable soluble carbon donors include food-processing wastes, paper processing wastes, grain dust, molasses residues, bagasse, and various residues of the fossil fuel industry including coal dust, refinery coke, and tar wastes.

Thus depending upon the loading of soluble organics in the wet methanol, 25% to 60% more heat is delivered to the combustion chamber and can be utilized more efficiently by fuel injectors or multi-fuel injectors as multi stacks of stratified combustants to combust more rapidly and eliminate particulates and oxides of nitrogen by adaptively controlled timing of the initial fuel injection and ignition, timing of each subsequent fuel injection and ignition and the fuel pressure of each fuel injection.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this application.

To the extent not previously incorporated herein by reference, the present application incorporates by reference in their entirety the subject matter of each of the following materials: U.S. patent application Ser. No. 12/857,553, filed on Aug. 16, 2010, now U.S. Pat. No. 8,940,265, and titled SUSTAINABLE ECONOMIC DEVELOPMENT THROUGH INTEGRATED PRODUCTION OF RENEWABLE ENERGY, MATERIALS RESOURCES, AND NUTRIENT REGIMES; U.S. patent application Ser. No. 12/857,541, filed on Aug. 16, 2010, now U.S. Pat. No. 9,231,267, and titled SYSTEMS AND METHODS FOR SUSTAINABLE ECONOMIC DEVELOPMENT THROUGH INTEGRATED FULL SPECTRUM PRODUCTION OF RENEWABLE ENERGY; U.S. patent application Ser. No. 12/857,554, filed on Aug. 16, 2010, now U.S. Pat. No. 8,808,529, and titled SYSTEMS AND METHODS FOR SUSTAINABLE ECONOMIC DEVELOPMENT THROUGH INTEGRATED FULL SPECTRUM PRODUCTION OF RENEWABLE MATERIAL RESOURCES USING SOLAR THERMAL; U.S. patent application Ser. No. 12/857,502, filed on Aug. 16, 2010, now U.S. Pat. No. 9,097,152, and titled ENERGY SYSTEM FOR DWELLING SUPPORT; U.S. patent application Ser. No. 13/027,235, filed on Feb. 14, 2011, now U.S. Pat. No. 8,313,556, and titled DELIVERY SYSTEMS WITH IN-LINE SELECTIVE EXTRACTION DEVICES AND ASSOCIATED METHODS OF OPERATION; U.S. Patent Application No. 61/401,699, filed on Aug. 16, 2010 and titled COMPREHENSIVE COST MODELING OF AUTOGENOUS SYSTEMS AND PROCESSES FOR THE PRODUCTION OF ENERGY, MATERIAL RESOURCES AND NUTRIENT REGIMES; U.S. patent application Ser. No. 13/027,208, filed on Feb. 14, 2011, now U.S. Pat. No. 8,318,131, and titled CHEMICAL PROCESSES AND REACTORS FOR EFFICIENTLY PRODUCING HYDROGEN FUELS AND STRUCTURAL MATERIALS, AND ASSOCIATED SYSTEMS AND METHODS; U.S. patent application Ser. No. 13/026,996, filed on Feb. 14, 2011, now U.S. Pat. No. 9,206,045, and titled REACTOR VESSELS WITH TRANSMISSIVE SURFACES FOR PRODUCING HYDROGEN-BASED FUELS AND STRUCTURAL ELEMENTS, AND ASSOCIATED SYSTEMS AND METHODS; U.S. patent application Ser. No. 13/027,015, filed on Feb. 14, 2011 and titled CHEMICAL REACTORS WITH RE-RADIATING SURFACES AND ASSOCIATED SYSTEMS AND METHODS; U.S. patent application Ser. No. 13/027,244, filed on Feb. 14, 2011 and titled THERMAL TRANSFER DEVICE AND ASSOCIATED SYSTEMS AND METHODS; U.S. patent application Ser. No. 13/026,990, filed on Feb. 14, 2011, now U.S. Pat. No. 8,187,549, and titled CHEMICAL REACTORS WITH ANNULARLY POSITIONED DELIVERY AND REMOVAL DEVICES, AND ASSOCIATED SYSTEMS AND METHODS; U.S. patent application Ser. No. 13/027,181, filed on Feb. 14, 2011, now U.S. Pat. No. 8,187,550, and titled REACTORS FOR CONDUCTING THERMOCHEMICAL PROCESSES WITH SOLAR HEAT INPUT, AND ASSOCIATED SYSTEMS AND METHODS; U.S. patent application Ser. No. 13/027,215, filed on Feb. 14, 2011, now U.S. Pat. No. 8,318,269, and titled INDUCTION FOR THERMOCHEMICAL PROCESS, AND ASSOCIATED SYSTEMS AND METHODS; U.S. patent application Ser. No. 13/027,198, filed on Feb. 14, 2011, now U.S. Pat. No. 9,188,086, and titled COUPLED THERMOCHEMICAL REACTORS AND ENGINES, AND ASSOCIATED SYSTEMS AND METHODS; U.S. Patent Application No. 61/385,508, filed on Sep. 22, 2010 and titled REDUCING AND HARVESTING DRAG ENERGY ON MOBILE ENGINES USING THERMAL CHEMICAL REGENERATION; U.S. patent application Ser. No. 13/027,060, filed on Feb. 14, 2011, now U.S. Pat. No. 8,318,100, and titled REACTOR VESSELS WITH PRESSURE AND HEAT TRANSFER FEATURES FOR PRODUCING HYDROGEN-BASED FUELS AND STRUCTURAL ELEMENTS, AND ASSOCIATED SYSTEMS AND METHODS; U.S. Patent Application No. 61/237,419, filed on Aug. 27, 2009 and titled CARBON SEQUESTRATION; U.S. patent application Ser. No. 13/027,068, filed on Feb. 14, 2011, now U.S. Pat. No. 8,318,997, and titled CARBON-BASED DURABLE GOODS AND RENEWABLE FUEL FROM BIOMASS WASTE DISSOCIATION; U.S. patent application Ser. No. 13/027,196, filed on Feb. 14, 2011, now U.S. Pat. No. 8,912,239, and titled CARBON RECYCLING AND REINVESTMENT USING THERMOCHEMICAL REGENERATION; U.S. Patent Application No. 61/237,425, filed on Aug. 27, 2009 and titled OXYGENATED FUEL PRODUCTION; U.S. patent application Ser. No. 13/027,197, filed on Feb. 14, 2011, now U.S. Pat. No. 8,070,835, and titled MULTI-PURPOSE RENEWABLE FUEL FOR ISOLATING CONTAMINANTS AND STORING ENERGY; U.S. Patent Application No. 61/421,189, filed on Dec. 8, 2010 and titled LIQUID FUELS FROM HYDROGEN, OXIDES OF CARBON, AND/OR NITROGEN; AND PRODUCTION OF CARBON FOR MANUFACTURING DURABLE GOODS; and U.S. patent application Ser. No. 13/027,185, filed on Feb. 14, 2011, now U.S. Pat. No. 8,328,888, and titled ENGINEERED FUEL STORAGE, RESPECIATION AND TRANSPORT.

I claim:

1. A method of producing an oxygenated fuel from biomass waste for use in a combustion system, the method comprising:

dissociating the biomass waste to produce one or more carbon donors;

filtering the biomass waste produced carbon donors through a filtration system to remove sulfurous substances;

reacting the biomass waste produced and filtered carbon donors with an oxygen donor to produce the oxygenated fuel comprising oxygenated carbon, wherein the reacting comprises:

applying energy recovered from an external energy source to the reaction of carbon donors and oxygen donor; and combusting the oxygenated fuel in the combustion system.

2. The method of claim 1, wherein the one or more carbon donors comprise carbon; and wherein the reacting comprises partially oxidizing the carbon to produce carbon monoxide and carbon dioxide.

3. The method of claim 1, wherein the one or more carbon donors comprise hydrocarbon and alcohol and the oxygen donor comprises steam; and wherein the reacting comprises reacting the hydrocarbon and alcohol with the steam to produce carbon monoxide and hydrogen.

4. The method of claim 1 wherein combusting the oxygenated carbon in the combustion system comprises:

providing an oxidant and the oxygenated fuel in a combustion zone of the combustion system.

5. The method of claim 1 further comprising:

controlling timing or duration of fuel injection using adaptive control.

6. The method of claim 1, further comprising:

controlling a fuel delivery pressure using adaptive control.

7. The method of claim 1, wherein the combustion system comprises a stratified-charge combustion system.

8. A method of producing an oxygenated fuel from biomass waste for use in a combustion system, the method comprising:

dissociating the biomass waste under an anaerobic reaction to produce the oxygenated fuel comprising oxygenated carbon and hydrogen, wherein the dissociating under the anaerobic reaction comprises:

applying waste heat recovered from an external heat source to the biomass waste, producing hydrocarbon and alcohol in addition to oxygenated carbon, and reacting the hydrocarbon and alcohol with an oxygen donor in the presence of the waste heat to generate additional oxygenated carbon; and combusting the oxygenated fuel in the combustion system.

9. The method of claim 8, wherein dissociating the biomass waste under the thermochemical reaction comprises producing carbon in addition to oxygenated carbon; and reacting the carbon with an oxygen donor in the presence of waste heat to generate additional oxygenated carbon.

10. The method of claim 8, wherein combusting the oxygenated carbon in the charge combustion system comprises:

providing multiple layers of an oxidant and the oxygenated fuel in a combustion zone of the combustion system.

11. The method of claim 10 further comprising:

controlling timing or a duration of fuel injection using adaptive control.

12. The method of claim 10 further comprising:

controlling fuel delivery pressure in the charge combustion system.

13. The method of claim 8, wherein the combustion system comprises a stratified-charge combustion system.

14. A method of recycling carbon to produce a renewable fuel, the method comprising:

harvesting carbon dioxide emitted from an industrial process;

dissociating biomass waste under an anaerobic reaction to produce hydrogen;

reacting the harvested carbon dioxide with the biomass waste produced hydrogen under pressure and heat to generate a renewable source of energy comprising hydrogen and carbon monoxide; and separating the hydrogen from the carbon monoxide by diffusing the generated renewable source of energy through a membrane in a separator.

15. The method of claim 14, wherein the heat used in reacting the harvested carbon dioxide with the biomass waste produced hydrogen comprises waste heat recovered from an external heat source.

16. The method of claim 14, wherein the combustion system comprises a stratified-charge combustion system.

* * * * *